United States Patent
Saltzman

[11] 3,931,403
[45] Jan. 6, 1976

[54] ANTIMICROBIAL COMPOSITIONS
[75] Inventor: William H. Saltzman, New Rochelle, N.Y.
[73] Assignee: Intellectual Property Development Corporation, New Rochelle, N.Y.
[22] Filed: Nov. 14, 1974
[21] Appl. No.: 523,627

Related U.S. Application Data
[63] Continuation of Ser. No. 363,460, May 25, 1973, abandoned.

[52] U.S. Cl. .............. 424/238; 424/242; 424/243; 260/397.2
[51] Int. Cl.² .......................................... C07J 9/00
[58] Field of Search ................... 424/238; 260/397.2

[56] References Cited
UNITED STATES PATENTS
| | | | |
|---|---|---|---|
| 3,839,565 | 10/1974 | Saltzman | 424/238 |
| 3,852,440 | 12/1974 | Weigand | 424/238 |
| 3,856,953 | 12/1974 | Saltzman | 424/238 |

Primary Examiner—Elbert L. Roberts

[57] ABSTRACT

This invention relates to new antimicrobial, antibiotic and bacteriostatic compositions and to methods for their use. The novel compositions of this invention are comprised of an active ingredient of the formula:

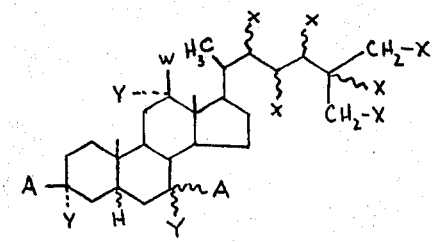

wherein
each Y is hydrogen;
each A is hydroxy, acyloxy or alkoxy;
W is hydrogen, hydroxy, acyloxy, or alkoxy;
A and Y when taken together, is oxo (O=);
W and Y when taken together, is oxo (O=);
each X is hydrogen, hydroxy, acyloxy or alkoxy, at least one X being hydroxy;

and the non-toxic, pharmaceutically acceptable salts thereof.

5 Claims, No Drawings

ANTIMICROBIAL COMPOSITIONS

This application is a continuation of any previously filed copending application Ser. No. 363,460, filed May 25, 1973 and now abandoned.

This invention relates to novel, physiologically active compositions which possess antimicrobial, antibiotic and bacteriostatic properties. More particularly, this invention relates to antimicrobial, antibiotic and bacteriostatic compositions having as their active ingredient a compound of the formula:

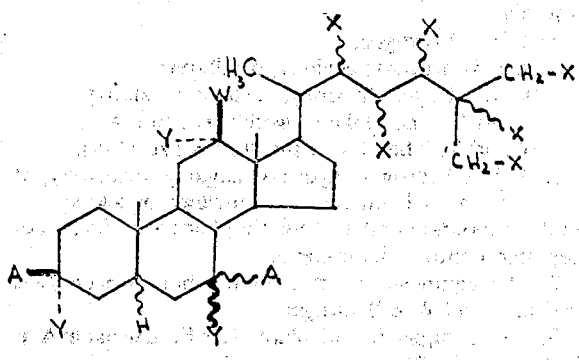

wherein
each Y is hydrogen;
each A is hydroxy, acyloxy, or alkoxy;
W is hydrogen, hydroxy, acyloxy, or alkoxy;
A and Y when taken together is oxo (O=);
W and Y when taken together is oxo (O=);
each X is hydrogen, hydroxy, acyloxy, or alkoxy, at least one X being hydroxy;
and the non-toxic pharmaceutically acceptable salts thereof.

The compositions of this invention possess antimicrobial, antibiotic and/or bacteriostatic properties and may be useful in the control of various microorganisms, especially certain anaerobic organisms. In addition, the compositions of this invention also appear to possess microorganism enzyme inactivation properties.

Among the compounds which may be utilized in the compostions of this invention may be included such compounds as $3\alpha,7\alpha,12\alpha,24,25$-pentahydroxy coprostane; $3\alpha,7\alpha,12\alpha,25$tetrahydroxy coprostane; $3\alpha,7\alpha,12\alpha$-triacyloxy-25-hydroxy coprostane; $3\alpha,7\alpha,12\alpha$-triacyloxy-24,25-dihydroxy coprostane; 3,7,12-triketo-24,25-dihydroxy coprostane; 3,7,12-triketo-25-hydroxy coprostane; $3\alpha,7\alpha$-dihydroxy-25-acyloxy coprostane; $3\alpha,7\alpha,25$-trihydroxy coprostane; $3\alpha,7\alpha,24,25$-tetrahydroxy coprostane; $3\alpha,7\alpha$-diacyloxy-25-hydroxy coprostane; $3\alpha,7\alpha$-diacyloxy-24,25-dihydroxy coprostane; $3\alpha,7\alpha12\alpha$-trialkoxy-25-hydroxy coprostane; $3\alpha,7\alpha,12\alpha$-trialkoxy-24,25-dihydroxy coporstane; scymnol; chimaerol; bufol; ranol; cyprinol; 27-deoxy cyprinol; $5\beta$-cholestane-$3\alpha,7\alpha,12\alpha,24$-tetrol; $5\beta$-cholestane-$3\alpha,7\alpha,12\alpha,24\alpha,25$-pentol $5\beta$-cholestane-$3\alpha,7\alpha,12\alpha,24\beta,25$-pentol; $5\beta$-cholestane-$3\alpha,7\alpha,12\alpha,25,26$-pentol; $5\beta$-cholestane-$3\alpha,7\alpha,12\alpha,2-5\alpha,26$-pentol; and other like compounds.

The compounds which may be employed in the practice of this invention may be prepared in accordance with methods and procedures known to the worker skilled in the art. As starting materials in the production of the compounds of this invention may be included such compounds as scymnol, $3\alpha,7\alpha$-dihydroxy coprostane, chenodeoxy-cholic acid, deoxycholic acid, varanic acid and cholic acid.

The preferred alkoxy radicals of the compounds of this invention are those which are comprised of six or less carbon atoms, and include such moieties as methyl, ethyl, propyl, butyl, pentyl, and hexyl.

The acyloxy radicals of the compounds of this invention are those from hydrocarbon carboxylic acids of less than twelve carbon atoms, and include such acids as the alkanoic acids, the alkenoic acids, the monocyclic aralkyl carboxylic acids, the monocyclic aryl carboxylic acids, the cycloalkane carboxylic acids, and the cycloalkene carboxylic acids.

Whenever in this application and the claims appended thereto, in any chemical structure set forth therein, a curved line (〜) is employed in the linkage of atoms, it is meant to denote that the connected atom or moiety may be in the alpha- or beta- position as the case may be. The compositions of this invention possess antimicrobial, antibiotic and/or bacteriostatic and/or bacterial enzyme inactivating activity and for this purpose may be administered to the patient suffering from such conditions as intestinal bacterial infections. The amount and the route of administration of the compositions of this invention can be adjusted by the skilled worker in accordance with the condition of the patient being treated and his requirements and the potency of the composition being employed. The compositions of this invention may be administered to the patient in any manner which may be deemed acceptable to the skilled worker practicing the invention. Most preferably, the compositions of this invention may be administered perorally to the patient being treated. For this purpose, the compositions of this invention may be prepared in such suitable pharmaceutically acceptable final dosage forms as may be employed by the skilled worker. Thus, commonly employed pharmaceutically acceptable dosage forms suitable for oral administration containing the active compounds of this invention in sufficient concentration to attain the desired results may be utilized. Pharmaceutically acceptable non-toxic inert carriers which are usually employed for such purposes may be utilized to prepare such dosage forms as tablets, capsules, elixirs, solutions, suspensions and the like. Satisfactory results in the practice of this invention may be obtained by the administration of small but effective amounts of the compositions and compounds of this invention to the patient being treated. Satisfactory results may be obtained when from 10 to 1500 mg. of the active compounds of this invention are daily administered to the patient being treated hereunder. In the use of tablet or capsule final dosage forms of the compositions of this invention, may be present from 10 to 500 mg of the compounds of this invention, although other concentrations may also provide satisfactory results.

The invention may be illustrated by the following examples:

EXAMPLE I

The compositions of this invention were prepared in the final dosage form of capsules containing the compounds in the concentrations set forth in Table A below:

Table A

| Compound | Concentration |
| --- | --- |
| 3α,7α,12α,24,25-pentahydroxy coprostane | 100 mg |
| 3α,7α,12α,25-tetra hydroxy coprostane | 100 mg |
| 3α, 7α, 25-trihydroxy coprostane | 100 mg |
| 3α, 7α, 24,25-tetrahydroxy coprostane | 100 mg |
| 5β-chlolestane-3α, 7α, 12α, 24α, 25-pentol | 100 mg |
| 5β-cholestane-3α, 7α, 12α, 24β, 25-pentol | 100 mg |
| 5β-cholestane-3α, 7α, 12α, 25, 26-pentol | 100 mg |

EXAMPLE II

5β-Cholestane-3α,7α,12α,25-tetrol, obtained in accordance with the disclosure of Pearlmen, 69 Journal of the American Chemical Society, 1475 et seq. (1947), was treated in accordance with the procedure of Hoshita, 52 Journal of Biochemistry 176 et seq. (1962) to yield 5β-cholestane-3α,7α,12α,24,25-pentol, m.p. 199°–200°C., which was then subjected to thin layer of chromatography. The 5β-cholestane-3α,7α,12α,24,25-pentol was applied as a band to a 0.25 mm thick Silica Gel G plate (Brinkmann) and the plate was developed with a chloroform: acetone: methanol (35:25:7.5 v/v/v) system, and the resulting bands visualized with iodine vapor. The more polar band (R 0.30) was 5β-cholestane-3α,7α,12α,24α,25-pentol, and the less polar band (R 0.34) was 5β-cholestane-3α,7α, 12α,24β,25-pentol.

The invention may be variously otherwise embodied within the scope of the appended Claims.

What is claimed is:

1. A composition possessing antimicrobial properties, comprising from about 10 to 1500 milligrams of a compound of the formula:

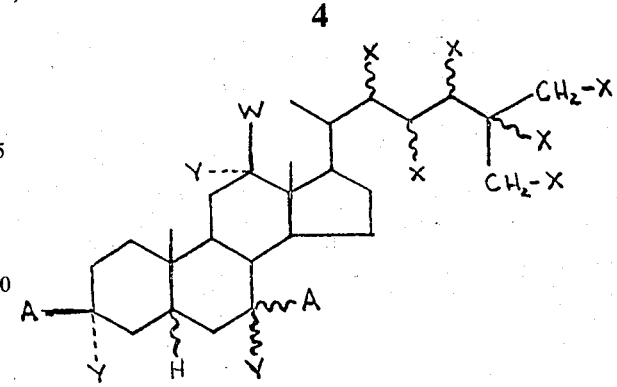

wherein
  each Y is hydrogen;
  each A is hydroxy, acyloxy, or alkoxy;
  W is hydrogen, hydroxy, acyloxy, or alkoxy;
  A and Y, when taken together is oxo (O=);
  W and Y, when taken together is oxo (O=);
  each X is hydrogen, hydroxy, acyloxy, or alkoxy, at least one X being hydroxy, acyloxy, or alkoxy;
said compound combined with a pharmaceutically acceptable nontoxic inert carrier.

2. The composition of claim 1, wherein each A is hydroxy, and W is hydrogen

3. The composition of claim 1, wherein each A is hydroxy, and W is hydroxy.

4. The composition of claim 1, wherein the compound is 3α,7α,12α,25-tetrahydroxy coprostane.

5. The composition of claim 1, wherein the compound is 3α,7α,12α,24,25-pentahydroxy coprostane.

* * * * *